United States Patent
Guillard et al.

(10) Patent No.: US 6,881,758 B2
(45) Date of Patent: Apr. 19, 2005

(54) PROCESS AND APPARATUS FOR THE PRODUCTION OF METHANOL

(75) Inventors: Alain Guillard, Paris (FR); Emmanuel Schmidt, Vincennes (FR)

(73) Assignee: L'Air Liquide - Societe Anonyme a Directoire et Conseil de Surveillance pour l'Etude et l'exploitation des Procedes Georges Claude, Paris (FR)

(*) Notice: Subject to any disclaimer, the term of this patent is extended or adjusted under 35 U.S.C. 154(b) by 48 days.

(21) Appl. No.: 10/773,223

(22) Filed: Feb. 9, 2004

(65) Prior Publication Data

US 2004/0176482 A1 Sep. 9, 2004

Related U.S. Application Data

(60) Provisional application No. 60/451,630, filed on Mar. 5, 2003.

(51) Int. Cl.$^7$ ................................................. C07C 27/00
(52) U.S. Cl. ........................ 518/700; 518/702; 518/703; 518/705
(58) Field of Search ................................ 518/700, 702, 518/703, 705

(56) References Cited

U.S. PATENT DOCUMENTS

| | | | |
|---|---|---|---|
| 3,962,300 A | 6/1976 | Hiller et al. | |
| 4,271,086 A | 6/1981 | Supp et al. | |
| 4,833,171 A | 5/1989 | Sweeney | |
| 4,910,228 A | 3/1990 | Lywood | |
| 5,177,114 A | * 1/1993 | Van Dijk et al. | 518/703 |
| 5,180,570 A | 1/1993 | Lee et al. | |
| 5,496,859 A | 3/1996 | Fong et al. | |

* cited by examiner

*Primary Examiner*—J. Parsa
(74) *Attorney, Agent, or Firm*—Young & Thompson

(57) ABSTRACT

In a process-for the use of a hydrocarbon feedstock (10) by reacting the feedstock in a reactor (11) with oxygen (9) to form a synthesis gas containing at least carbon monoxide, carbon dioxide and hydrogen and subjecting the synthesis gas to a conversion process comprising an exothermic reaction to produce methanol as a final product in a converter (15), the converter operating at an operating pressure, said oxygen being provided to the reactor at an oxygen pressure, the synthesis gas is produced at a pressure higher than the operating pressure of the converter.

12 Claims, 1 Drawing Sheet

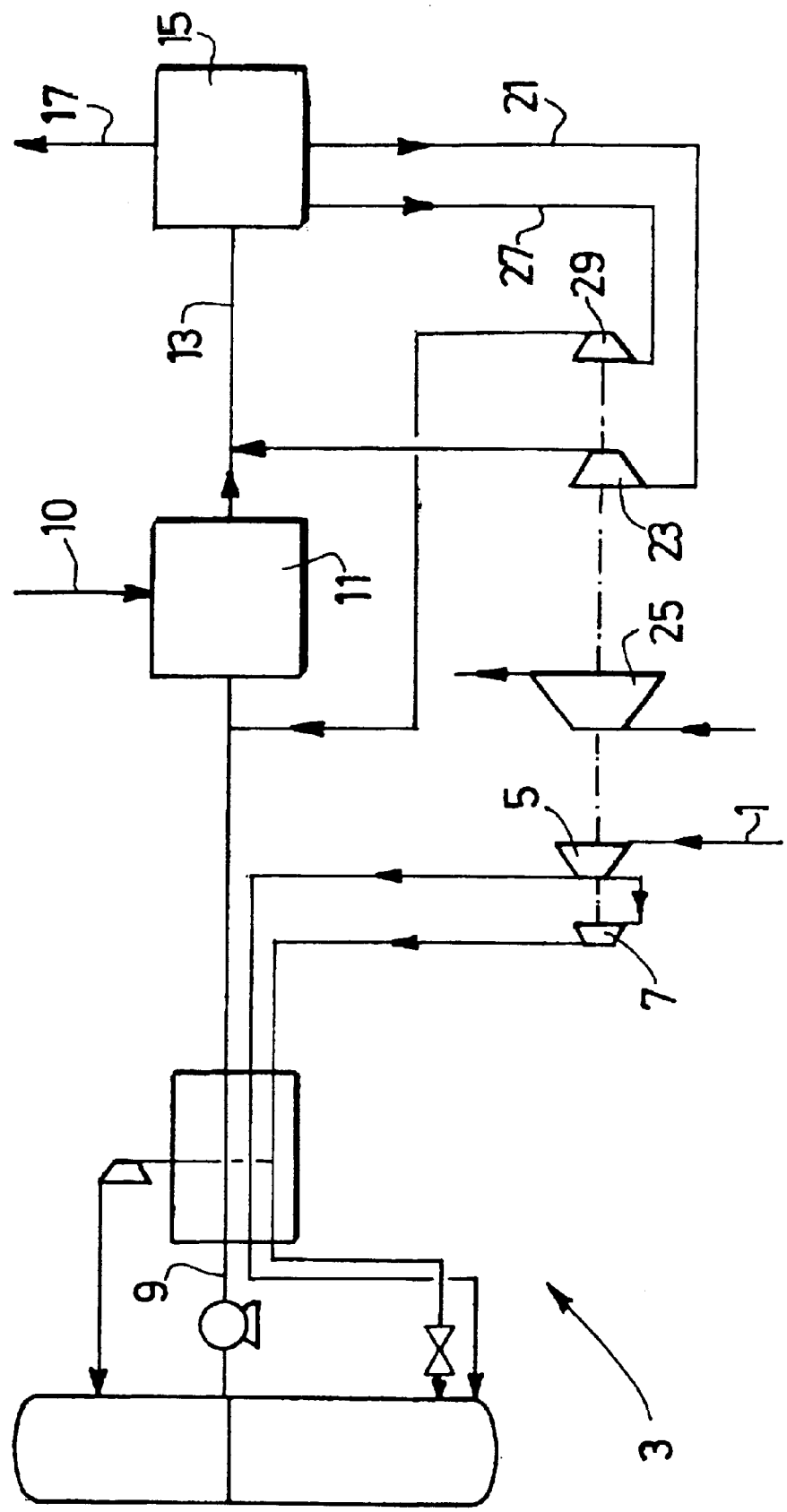

PROCESS AND APPARATUS FOR THE PRODUCTION OF METHANOL

TECHNICAL FIELD OF THE INVENTION

The present invention relates to a process and apparatus for the production of methanol.

All the pressures mentioned are absolute pressures.

BACKGROUND OF THE INVENTION

Methanol is produced by contacting a synthesis gas containing at least carbon monoxide, carbon dioxide and hydrogen with a catalyst. This synthesis gas is converted to methanol in a separate vessel. The synthesis gas can be produced either by reforming a hydrocarbon with steam or by reacting hydrocarbons with oxygen or by a mixture of these two technologies used in series or in parallel. The syngas produced in the syngas production unit or units is then compressed with a syngas compressor before being converted to methanol in a converter which is operated at a high pressure in the range of 80–120 bar. The unreacted syngas is then compressed in a syngas recycle compressor, mixed with the syngas coming from the syngas production unit and the mixed stream is sent to the inlet of the methanol converter. The methanol is recovered and purified in a methanol recovery unit made essentially of two or three distillation columns in order to reach the required methanol purity.

Since methanol is produced at high pressures in the range of 65–120 bar, the main process steps usually include syngas production, syngas compression, methanol synthesis and methanol recovery. When oxygen is used to produce synthesis gas, there is an air separation unit upstream of the syngas production unit.

The current trend is to produce methanol in very large quantities, five thousand tonnes of methanol per day or more. Large methanol plants require large syngas production units and the trend is to use oxygen-based technologies in order to produce these large quantities of syngas in a single train unit and to increase the energy efficiency of the overall methanol production process. Alternatively, it is possible to produce large quantities of syngas without using oxygen by injecting large quantities of carbon dioxide in the synthesis gas production unit. The carbon dioxide may come from various sources such as the carbon dioxide present at the outlet of the methanol converter or the carbon dioxide made in nearby ammonia production units or the carbon dioxide naturally present in natural gas. With a large $CO_2$ injection, it is possible to reach an energy efficiency comparable to those obtained with oxygen-based schemes. Most of these processes use an air separation unit (ASU) to produce oxygen at high pressure to convert natural gas to synthesis gas, the synthesis gas being sent to a single converter where it is converted to methanol.

As described in U.S. Pat. No. 6,117,916, an ASU produces oxygen at 40 bar and the oxygen reacts with steam and natural gas in a partial oxidation reactor to produce synthesis gas. The synthesis gas at 40 bar is then compressed to 70 bar and is sent to a methanol reactor, thereby producing methanol at 66 bar.

Usually two synthesis gas compressors in parallel are used to avoid maintenance problems. These compressors are costly both in capital investment and in terms of upkeep.

SUMMARY OF THE INVENTION

According to an object of this invention, in a process for the use of a hydrocarbon feedstock by reacting the feedstock in a reactor with oxygen to form a synthesis gas containing at least carbon monoxide, carbon dioxide and hydrogen and subjecting the synthesis gas to a conversion process comprising an exothermic reaction to produce methanol as a final product in a converter, the converter operating at an operating pressure, said oxygen being provided to the reactor at an oxygen pressure following separation of cooled compressed air, compressed in an least one air compressor, the improvement consisting in that the synthesis gas is produced at a pressure such that the synthesis gas is sent from the reactor to the converter without undergoing a compression step, and the air separation unit supplies oxygen to the reactor at an oxygen pressure greater than the operating pressure of the reactor.

The synthesis gas is produced at a pressure higher than the operating pressure of the converter at least1 bar higher, possibly at least 3 bar higher, or even at least 5 bar higher, than the operating pressure of the converter.

The hydrocarbon feedstock may be natural gas.

Some carbon dioxide may be present at the converter outlet; in this case carbon dioxide is recycled to an inlet of the reactor following compression in a carbon dioxide compressor. In addition some unreacted synthesis gas is present at the converter outlet and this may be recycled to the converter inlet following compression in a recycle synthesis gas compressor.

A steam turbine may be coupled to at least one of the recycle synthesis gas compressor, the carbon dioxide compressor, an air booster and an air compressor.

The reactor may be a partial oxidation reactor or an autothermal reactor.

The air separation unit produces oxygen at an oxygen pressure greater than the operating pressure of the reactor, preferably at least 5 bar greater than the operating pressure of the reactor, more possibly at least 3 bar greater than the operating pressure of the reactor, possibly at least 1 bar greater than the operating pressure of the reactor.

According to a further aspect of the invention, in an apparatus for the use of a hydrocarbon feedstock by reacting the feedstock in a reactor with oxygen to form a synthesis gas containing at least carbon monoxide, carbon dioxide and hydrogen: a reactor, means for sending the feedstock and oxygen to the reactor, means for removing synthesis gas from the reactor, means for subjecting the synthesis gas to a conversion process comprising an exothermic reaction in a converter, the converter operating at an operating pressure, said oxygen being provided by air separation at an oxygen pressure; the improvement consisting in that there is no synthesis gas compressor for compressing the synthesis gas which is produced by the reactor which is to be sent to the converter.

The apparatus may comprise a recycle synthesis gas compressor for compressing recycle synthesis gas sent from the converter to upstream the converter.

The apparatus may comprise a carbon dioxide compressor for compressing recycle carbon dioxide gas sent from the converter to upstream the reactor.

A steam turbine may be being coupled to at least one of the synthesis gas compressor, the carbon dioxide compressor, at least one air compressor for compressing air to be separated to form oxygen and an at least one air booster.

BRIEF DESCRIPTION OF THE DRAWINGS

FIG. 1 is a schematic drawing of an installation according to the invention.

DETAILED DESCRIPTION OF THE INVENTION

The invention will now be described in greater detail with reference to the Figure.

Air 1 is separated in an ASU 3 which produces at least liquid oxygen. Any of the plants using a liquid oxygen vaporisation step by heat exchange with feed air as shown in <<The Technology of Catalytic Oxidations >>by Arpentinier et al., Editions Technip, 2001 or <<Tieftemperaturtechnik >>by Hausen Linde may be used. The air is compressed to 6 bar in compressor 5, purified in adsorbent beds (not shown) and then sent in part to a column of the ASU. Another part of the compressed air is pressurized in a booster 7 to a pressure of 70 bar. The air is expanded, then partially liquefied and is sent either entirely to the medium pressure column as shown or at least in part to the low pressure column. The usual reflux streams are not shown for the sake of simplicity. The heat exchanger serves to warm gaseous streams (not shown) from the columns as well as at least one liquid stream 9. The liquid oxygen 9 is pumped to a pressure of 61 bar and vaporised by heat exchange with the feed air. The gaseous oxygen produced at 60 bar (following pressure drop in the exchanger and pipes) is sent to a reactor 11, which may be a partial oxidation reactor or an autothermal reactor having an entry pressure of 60 bar. The reactor 11 is also fed by natural gas 10 at 60 bar.

Where the operating pressure of the reactor is P, the oxygen is produced and sent to the reactor at a pressure of P +$\Delta$P, P being preferably at least 49 bar and $\Delta$P being greater than zero. The oxygen may be produced at between 50 and 80 bar, preferably above 60 bar or even 70 bar and sent to the reactor at that pressure for the case where the operating pressure of the reactor is 49 bar. The oxygen may either be pumped directly to a pressure between 50 and 80 bar and then vaporised at that pressure in the main heat exchange line or may be pumped to an intermediate pressure, vaporised at the intermediate pressure in the main heat exchange line and then compressed to a pressure between 50 and 80 bar in an oxygen compressor.

Synthesis gas is produced at a pressure of 60 bar and is sent at that pressure to the converter 15 via conduit 13. There is no compressor to compress the synthesis gas since the converter 15 operates with an entry pressure of 50 bar and there is an around 1 to 10 bar pressure drop between the entry of the reactor 11 and the entry of the converter 15 due to the presence of a boiler for raising steam and other devices (not shown).

The converter produces methanol as a final product 17. Unreacted synthesis gas 21 may be recycled from an outlet of the converter 15 to the inlet of the converter 15 following compression in compressor 23. It is also common to recycle carbon dioxide 27 from an outlet of the converter 15 to the inlet of the reactor 11 following compression in compressor 29. Preferably the compressor 5, the booster 7, the carbon dioxide recycle compressor 29 and the recycle synthesis gas compressor 23 are all driven by a single steam turbine 25, the steam being derived from the exothermic process. Failing this at least some of the above mentioned compressors are driven by a steam turbine. EP-A-1102953 describes a steam turbine which is used to drive a main air compressor and an air booster. It is of course possible for separate steam turbines to drive the recycle synthesis gas compressor, the carbon dioxide recycle compressor and one or both of the air compressors. The booster 7 is not an essential element of the air separation unit 3; it is for example possible for air compressor 5 to compress all the air to the vaporization pressure required to gasify the oxygen as described in EP-A-0504029. Since the conversion process is highly exothermic, this process or the synthesis gas may be used to raise steam for the steam turbine 25.

We claim:

1. In a process for the use of a hydrocarbon feedstock by reacting the feedstock in a reactor with oxygen to form a synthesis gas containing at least carbon monoxide, carbon dioxide and hydrogen and subjecting the synthesis gas to a conversion process comprising an exothermic reaction to produce methanol as a final product in a converter, the converter operating at an operating pressure, said oxygen being provided to the reactor at an oxygen pressure following separation of cooled compressed air compressed in at least one air compressor, the improvement consisting in that the synthesis gas is produced at a pressure such that the synthesis gas is sent from the reactor to the converter without undergoing a compression step, and the air separation unit supplies oxygen to the reactor at an oxygen pressure greater than the operating pressure of the reactor.

2. The process of claim 1 wherein the synthesis gas is produced at a pressure at least 1 bar higher than the operating pressure of the converter.

3. The process according to claim 1 wherein the hydrocarbon feedstock is natural gas.

4. The process according to claim 1 wherein methanol, and at least one of carbon dioxide and unreacted synthesis gas are present at the outlet of the converter.

5. The process according to claim 4 wherein carbon dioxide is present at the outlet of the converter and carbon dioxide produced by the converter is recycled to an inlet of the reactor following compression in a carbon dioxide compressor.

6. The process according to claim 5 wherein at least one of the carbon dioxide compressor and an air compressor and an air booster is coupled to a steam turbine.

7. The process according to claim 4 wherein unreacted synthesis gas is present at the outlet of the converter and unreacted synthesis gas produced by the converter is recycled to an inlet of the converter following compression in a recycle synthesis gas compressor.

8. The process according to claim 7 wherein at least one of the recycle synthesis gas compressor and an air compressor and an air booster is coupled to a steam turbine.

9. The process according to claim 1 wherein the hydrocarbon feedstock reacts with the oxygen in a partial oxidation reactor.

10. The process according to claim 1 wherein the hydrocarbon feedstock reacts with the oxygen in an autothermal reactor.

11. In an apparatus for the use of a hydrocarbon feedstock by reacting the feedstock in a reactor with oxygen to form a synthesis gas containing at least carbon monoxide, carbon dioxide and hydrogen: a reactor, a feedstock conduit for sending the feedstock to the reactor, an oxygen conduit for sending the oxygen to the reactor, a synthesis gas removal conduit for removing synthesis gas from the reactor, said synthesis gas removal conduit being connected to a converter for subjecting the synthesis gas to a conversion process comprising an exothermic reaction to produce methanol as a final product in a converter, the converter operating at an operating pressure; said oxygen being provided by air separation at an oxygen pressure, the improvement consisting in that there is no synthesis gas compressor for compressing the synthesis gas which is produced by the reactor and which is to be sent to the converter.

12. The apparatus according to claim 11 comprising a steam turbine and at least one of at least one air compressor for compressing air to be separated to form oxygen, at least one air booster for further compressing air to be separated to form oxygen, a carbon dioxide compressor for compressing carbon dioxide sent from the converter to the reactor and a recycle synthesis gas compressor for compressing unreacted synthesis gas sent from the converter to upstream the converter, said steam turbine being coupled to at least one of the recycle synthesis gas compressor, the carbon dioxide compressor and an at least one air compressor and an air booster.

* * * * *